United States Patent
Dimitrenko

(10) Patent No.: US 11,914,131 B1
(45) Date of Patent: Feb. 27, 2024

(54) OPTICAL TESTING SYSTEM FOR DETECTING INFECTIOUS DISEASE, TESTING DEVICE, SPECIMEN COLLECTOR AND RELATED METHODS

(71) Applicant: Gregory Dimitrenko, Woodstock, IL (US)

(72) Inventor: Gregory Dimitrenko, Woodstock, IL (US)

( * ) Notice: Subject to any disclaimer, the term of this patent is extended or adjusted under 35 U.S.C. 154(b) by 0 days.

(21) Appl. No.: 17/402,576

(22) Filed: Aug. 15, 2021

Related U.S. Application Data

(60) Provisional application No. 63/066,316, filed on Aug. 16, 2020.

(51) Int. Cl.
   *G02B 21/36* (2006.01)
   *A61B 5/15* (2006.01)
   (Continued)

(52) U.S. Cl.
   CPC ........ *G02B 21/36* (2013.01); *A61B 5/150022* (2013.01); *A61B 10/0045* (2013.01); *A61B 10/0051* (2013.01); *A61B 10/007* (2013.01); *G01N 21/3577* (2013.01); *G01N 33/48778* (2013.01); *G02B 21/084* (2013.01); *G06T 7/0014* (2013.01); *C12Q 1/6816* (2013.01); *C12Q 2565/601* (2013.01);
   (Continued)

(58) Field of Classification Search
   CPC ...... G02B 21/36; G02B 21/084; G02B 21/00; A61B 5/150022; A61B 10/0045; A61B 10/0051; G01N 33/48778; G01N 33/56983; G06T 7/0014; G06T 2207/10056; C12Q 1/6816; C12Q 2565/601; B01L 2300/0636; B01L 2200/10
   See application file for complete search history.

(56) References Cited

U.S. PATENT DOCUMENTS 5,062,697 A * 11/1991 Mitchell ............ G02B 21/0008
                                                     359/398
6,060,022 A *  5/2000 Pang .................. G01N 35/0095
                                                      422/65
(Continued)

FOREIGN PATENT DOCUMENTS

EP        2764918 A1 *  8/2014  ......... A61B 10/0045
WO    WO-9847429 A1 * 10/1998  ......... A61B 10/0012
(Continued)

*Primary Examiner* — Sean P Dougherty

(57) ABSTRACT

A testing system (10) for an infectious disease, such as Covod-19, has a specimen collector (11) with a housing (12) receiving a specimen of bodily fluids discharged from a cough of a test subject through a specimen inlet (15). After specimen collection, the specimen inlet (15) is closed, and the collector (11) is brough to a mating electronic testing device (13). A seal (55) is removed to expose a transparent specimen tray (43) upon which the specimen has fallen and installed into a collector receptacle (14). A microscope (15) is focused on the specimen, Photographs of the specimen are taken through a microscope (15) and then compared to photographs of specimens known to have indications of infection (26). Based on the comparison, a test result and level of confidence is obtained. The collector (11) is then removed from the testing device (13), and discarded.

15 Claims, 12 Drawing Sheets

(51) Int. Cl.
*A61B 10/00* (2006.01)
*C12Q 1/6816* (2018.01)
*G01N 21/3577* (2014.01)
*G01N 33/487* (2006.01)
*G01N 33/569* (2006.01)
*G02B 21/00* (2006.01)
*G02B 21/08* (2006.01)
*G06T 7/00* (2017.01)

(52) U.S. Cl.
CPC ........ *G01N 33/56983* (2013.01); *G02B 21/00* (2013.01); *G06T 2207/10056* (2013.01); *G06T 2207/30024* (2013.01)

(56) References Cited

U.S. PATENT DOCUMENTS

| | | | | |
|---|---|---|---|---|
| 7,564,623 | B2* | 7/2009 | Vodyanoy | G02B 21/16 359/368 |
| 9,602,777 | B2* | 3/2017 | Winkelman | G06K 9/00 |
| 10,746,665 | B2* | 8/2020 | Kluckner | G06T 7/143 |
| 11,047,845 | B1* | 6/2021 | Barry, Jr. | G01N 33/49 |
| 11,137,391 | B2* | 10/2021 | Burd | G01N 33/5304 |
| 11,163,673 | B1* | 11/2021 | Meier | G06F 11/3466 |
| 2001/0008614 | A1* | 7/2001 | Aronowitz | A61J 1/05 436/178 |
| 2003/0170613 | A1* | 9/2003 | Straus | G01N 33/56983 435/5 |
| 2004/0114788 | A1* | 6/2004 | Nakazawa | H01J 37/26 250/311 |
| 2004/0135083 | A1* | 7/2004 | Kakibayashi | H01J 37/22 250/311 |
| 2005/0051725 | A1* | 3/2005 | Nakagaki | G01N 23/04 250/311 |
| 2009/0069639 | A1* | 3/2009 | Linssen | G01N 15/12 600/300 |
| 2010/0241019 | A1* | 9/2010 | Varga | A61B 5/082 600/532 |
| 2012/0075325 | A1* | 3/2012 | Kurtyka | G06F 16/58 345/589 |
| 2012/0075626 | A1* | 3/2012 | Geva | B01F 33/452 356/244 |
| 2012/0078524 | A1* | 3/2012 | Stewart | G16H 50/70 702/19 |
| 2012/0106811 | A1* | 5/2012 | Chen | B01L 3/5023 422/402 |
| 2012/0169863 | A1* | 7/2012 | Bachelet | G01N 21/23 348/79 |
| 2012/0282681 | A1* | 11/2012 | Teixeira | G01N 1/38 435/287.2 |
| 2013/0209993 | A1* | 8/2013 | Aronowitz | B01L 3/5021 435/5 |
| 2013/0239527 | A1* | 9/2013 | Clarke | B67B 7/02 53/381.1 |
| 2013/0299694 | A1* | 11/2013 | Sato | A61B 10/0045 250/288 |
| 2014/0222443 | A1* | 8/2014 | Danenberg | C12Q 1/6886 705/2 |
| 2014/0242682 | A1* | 8/2014 | Curry | G01N 33/5308 435/287.2 |
| 2014/0294698 | A1* | 10/2014 | Hershey | B01L 3/502 422/547 |
| 2015/0036138 | A1* | 2/2015 | Watson | G01N 21/65 356/402 |
| 2015/0064080 | A1* | 3/2015 | Skakoon | A61B 10/0051 600/573 |
| 2015/0140563 | A1* | 5/2015 | Conoci | C12Q 1/6851 29/458 |
| 2016/0186266 | A1* | 6/2016 | Alarcon | G01N 33/57484 702/20 |
| 2016/0306934 | A1* | 10/2016 | Sperry | C12Q 1/04 |
| 2016/0363753 | A1* | 12/2016 | Todd | F21V 23/003 |
| 2017/0218436 | A1* | 8/2017 | Azimi | G01N 33/57415 |
| 2018/0214880 | A1* | 8/2018 | Ketner | B01L 9/50 |
| 2019/0041302 | A1* | 2/2019 | Hunt | G01N 1/2813 |
| 2019/0187048 | A1* | 6/2019 | Wood | G01N 21/65 |
| 2019/0261960 | A1* | 8/2019 | Lee | G06T 7/0012 |
| 2019/0287149 | A1* | 9/2019 | Papp | G06Q 20/322 |
| 2021/0290975 | A1* | 9/2021 | Hunter | A61N 5/0624 |
| 2021/0291162 | A1* | 9/2021 | Saukkonen | B01L 3/508 |
| 2021/0345994 | A1* | 11/2021 | Green | B01L 3/5023 |
| 2021/0350877 | A1* | 11/2021 | Spurbeck | B01L 3/502784 |
| 2021/0373015 | A1* | 12/2021 | Johnson | G01N 33/56911 |
| 2021/0402394 | A1* | 12/2021 | Sievers-Engler | B01L 3/502715 |

FOREIGN PATENT DOCUMENTS

| | | | | |
|---|---|---|---|---|
| WO | WO-2013138208 | A1* | 9/2013 | ......... G01N 23/2251 |
| WO | WO-2014179215 | A1* | 11/2014 | ............. A61B 10/00 |
| WO | WO-2015057089 | A1* | 4/2015 | ........... A61B 10/0051 |

* cited by examiner

OPTICAL TESTING SYSTEM FOR DETECTING INFECTIOUS DISEASE, TESTING DEVICE, SPECIMEN COLLECTOR AND RELATED METHODS

CROSS-REFERENCE TO RELATED APPLICATION

This application is based on, and claims the benefits under, 35 USC 119(e) of provisional patent application Ser. No. 63/066,316, of the present inventor, filed Aug. 16, 2020, which is hereby incorporated by reference.

BACKGROUND OF THE INVENTION

Field of the Invention

This invention generally relates to an infectious disease testing system, and more particularly, to such a system in which specimens of bodily fluids are optically examined signifying the test subject is infected with one or more infectious pathogens.

Discussion of the Prior Art

There are numerous ways through medical science tests patients to determine whether they have an infectious disease.

While they all have relative advantages or disadvantages, of then their biggest failing relates to delay time.

First, there is the delay in the time it takes to have the test conducted, in the first instance. Most testing of Covid-19 required the test subject to travel to a testing cite and, depending upon circumstances, have to wait in line for long periods. Many persons due to work, lack of transportation, infirmity, etc. who should have been tested promptly and wanted to be tested promptly, could not be tested promptly, if at all. Nurses and others qualified to administer tests could go to elderly care facilities, but such qualified persons were not plentiful and appointments had to be made weeks in advance.

Second, the delay is the "test results delay time", which is the time from when that the test subject is final able to be tested, until the result of the test is determined and made available, so the test subject who can take necessary precautions, accordingly. Test results delay time can be hours or days.

Knowledge is power, and lack of knowledge of being infected resulted in rapid and wide spread of Covid-19 amongst the world population. Responsible persons, who would have taken the test, been made aware of their infection, would have self-isolated themselves until the period of infection transmission was over, same delays who spread it to another, etc. until there was a pandemic infecting the entire population of the world that may never be contained.

What was needed was a testing system that was readily available and gave prompt results to eliminate test result delay.

SUMMARY OF THE INVENTION

It is therefore an object of the present invention to provide a testing system for detecting whether a test subject is infected with an infectious pathogen that eliminates the problems associated with current systems discussed above.

Unlike many testing systems noted above, there are no test result delays, no test scheduling problems, no test location inconvenience problems and no need for trained test administrators.

All that is required is the discharge of self-administered cough into the interior of a small handheld collector and then manually mating the collector with readily movable testing device and initiating a test cycle. Thee test results are available almost instantaneously. Medical training is not required to administer and interpret the test results.

There is no delay required for treatment of the specimen before the test can be performed. Immediate test results are virtually instantaneously. Since it is portable the user/owner can have a test conducted on themselves at any place for any reason.

This can make all the difference in reducing the spread of Covid-19 during a pandemic. Average citizens can immediately know whether they are infected and self-quarantine. Employers can test at the door and prevent employees hat test positive at the door from entering and spreading the disease to coworkers. Schools and colleges can block the infected students, teachers, staff, et al. from entering before they can spread infection. Athletic teams can test and get immediate results before practice and games. Theaters, restaurants, stadiums and other public indoor environments in which disease through air recirculation and lack of social distancing can prevent the spread of disease at the door. The pandemic could be stopped once all the persons infected knew immediately when they became infected and then put themselves into quarantine until no longer infectious.

In general, it is the objective of the present invention to save as many valuable lives, whoever, whatever or wherever they are, by providing a testing means of doing so.

More specifically, this main objective is will hopefully be obtained in part by providing an infectious disease testing system for determining whether a test subject is infected with a pathogen, having a specimen collector having a hollow body with a specimen receipt opening at a collection end of the hollow body for receiving, within the tubular body, a specimen of bodily fluids from the mouth of the test subject, an examination opening at an examination end of the hollow body located oppositely of the specimen receipt opening, a specimen collection tray carried by the hollow body adjacent the examination end, and a readily removable anticontamination seal attached to the examination end of the hollow body to protectively close the examination opening to protect the collection tray from contamination; and an electronic testing device having a housing, a microscope, an examination port hole for receipt of at least the examination end of the collector housing into an examination location at which the specimen can be viewed by the microscope, a microcomputer, either responsive to the visual images to determine whether they contain any indications of infectious disease, or capable of communicating with a remote computer having Al software, responsive to the visual images to determine whether they contain any indications of infectious disease, and means responsive to the microcomputers to provide an indication of the results of the test.

Additionally, the objective of the invention is acquired, in part, by provision of a method of using a medical testing system having a specimen collector having a hollow housing body with a specimen receipt opening at a collection end of the hollow body for receiving, within the hollow body, a specimen of bodily fluids from the mouth of the test subject, and an anticontamination collection closure member, an examination opening at an examination end of the hollow body located oppositely of the specimen receipt opening, and an anticontamination examination closure member, a readily removable anticontamination seal attached to the examination end of the hollow body to protectively close the examination opening to protect the collection tray from contamination, and adapted to fit into a specimen receiving port of an automated infectious disease testing device, performance of the steps of remove the collection closure member from the collector, have test subject cough into and through the specimen receiving port opening to pass bio fluids into the hollow body where it may be examined, retrieve the collector, promptly reinstall the collection closure member to close the specimen receiving port to prevent contamination of the interior of the hollow body, carry the specimen protectively contained within the hollow body of the collector to the testing device, when ready to immediately commence a test of the collected specimen, remove the anticontamination seal to enable viewing of the sample outside of the hollow body of the collector from the examination, promptly, after removing the seal to reduce the risk of contamination, install the collector into the collector receptacle of the testing device, commence test and observe test results and store or record test results.

A further objective of the invention is achieved in part by provision of an infectious disease testing device, having, a protective housing, an opening in the protective housing for passage of a specimen collector into receptacle for securely holding the specimen at a precise examination location, a receptacle opening in the outer wall for releasable receipt of the specimen collection insert into the receptacle, a light source within the housing for illuminating the specimen collection insert when received within the housing, means including a microscope for taking at least one high resolution digital photograph of the collected specimen, a specimen configuration memory for storing the at least one high resolution digital collected specimen photograph, a known pathogen configuration memory for storing a digital pictorial representation of an infection indicating specimen of a person known to have a particular infectious disease or a composite pooling of like photographs, means for comparing the digital photograph or photographs of the collected specimens known to associated with an infectious disease of interest with the photo specimen collection insert and discerned by the microscopic assembly, and means responsive to the comparing means for providing an indication of whether or not the known specimen is that a person with the disease of diseases for which the test or tests was conducted. corresponds to a configuration of any pathogen carried by the specimen collection insert, and means for indicating the results of the test.

An additional object of the present invention is to provide an oral specimen collector for collecting specimens of saliva by means of cough charge for later examination or diagnosis of possible infectious disease, having a hollow body with a specimen receipt opening at a collection end of the hollow body for receiving, within the tubular body, a specimen of bodily fluids from the mouth of the test subject, an examination opening at an examination end of the hollow body located oppositely of the specimen receipt opening, a specimen collection tray carried by the hollow body adjacent the examination end, and a readily removable anticontamination seal attached to the housing to seal it closed against contamination.

BRIEF DESCRIPTION OF THE DRAWINGS

The foregoing objects, features and advantages will be described and other objects, features and advantages will be made apparent from the following detailed description which us given with reference to the several figures of the drawing, in which:

FIG. 14 is a logic flow chart of operation of a test including shut down of the testing device after the test is completed.

DETAILED DESCRIPTION

Figure 1:
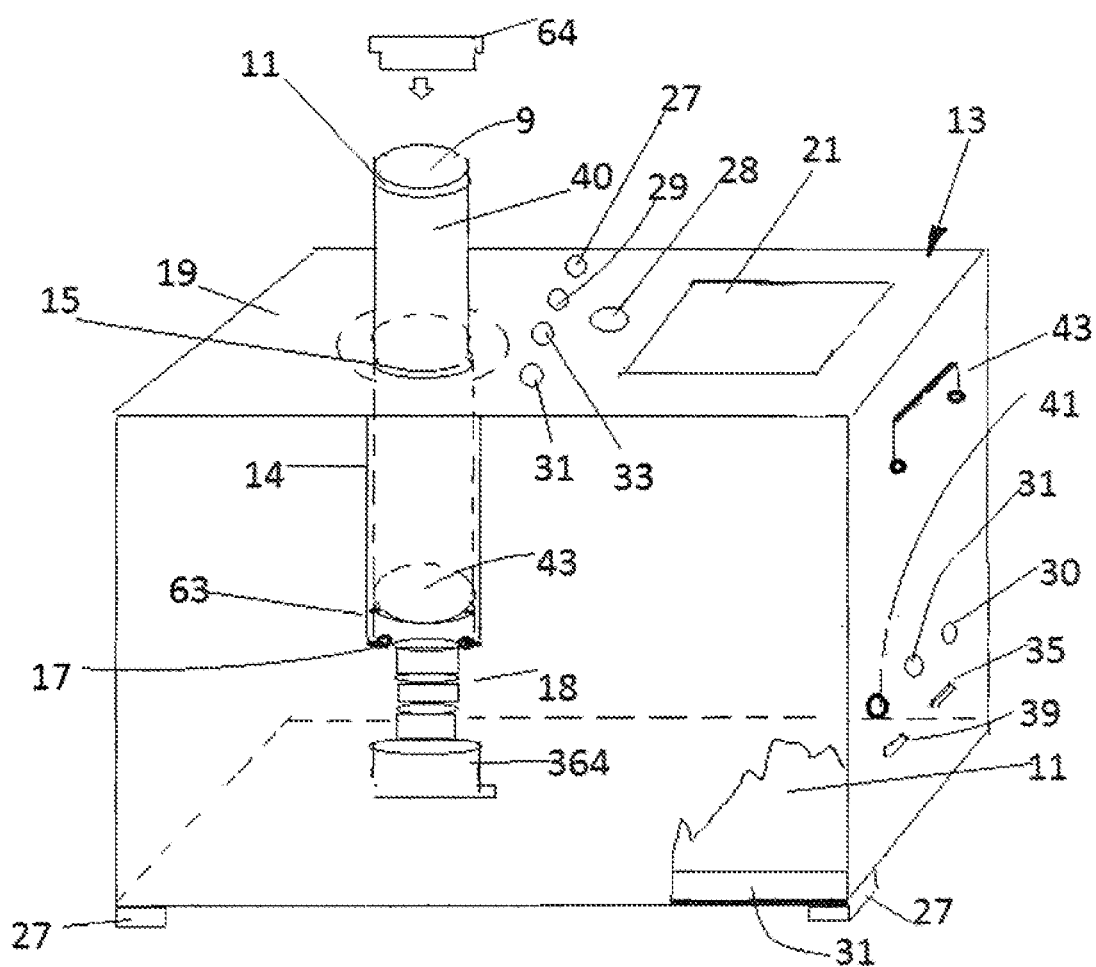
FIG. 1 is a perspective view of infectious disease testing system showing when a specimen collector of the system is installed into an examination receptacle of the testing device and ready for the optical specimen evaluation of the test.

Referring to FIG. 1, the infection testing device 10 of the present invention is comprised of two units: a specimen collection unit, or collector, 11 and a specimen testing unit 13. The collector 11 and the testing device 13 must be used together in cooperative engagement in order to accomplish a test. The tests conducted may are used to determine whether a test subject is infected with an infectious ease due to an infectious virus, such as pneumococcal, influenza or Covid-19 virus, an infectious bacterium, such a MRSA or an infectious mold spore such as.

Figure 2B:
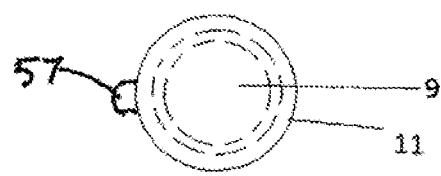
FIG. 2B is a plan view of the collector of FIG. 2 showing the contamination preventing closure cap covering the opening at the cough collection end of the collector.
Figure 2A:
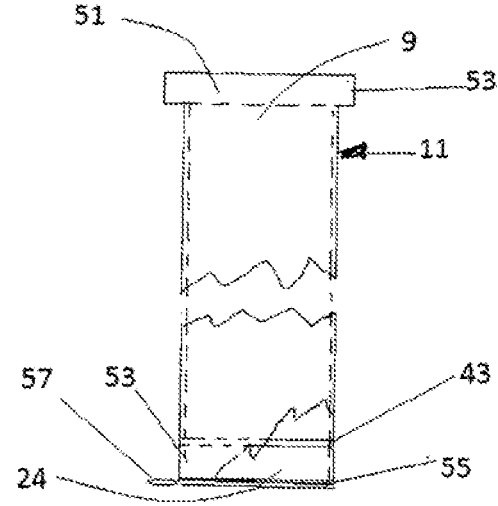
FIG. 2A is side elevation view of the tubular specimen collection insert 40 of FIG. 2 when removed from and shown apart from the housing 12, partially in section to reveal and internal specimen collection tray.
Figure 2C:
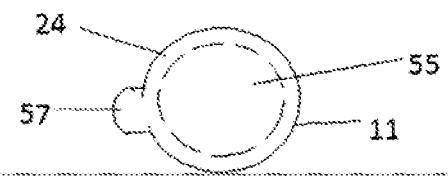
FIG. 2C is a bottom view of the collector FIGS. 2A showing the seal that closes the examination end of the collector of FIGS. 2A and 2B before the microscopic examination of the specimen collected on the examination tray of FIG. 2A after the specimen has been collected.

The collector, 11, which is used to collect a specimen of saliva, mucus or other oral from a test subject by having the test subject cough into an open collection end 9 of the collector 11, as will be illustrated below with respect to FIGS. 2A, 2B and 2C. After the specimen has been obtained, the collector 1 is used to carry the specimen to the testing device 13 and then inserted through collector receptacle entry port 15 in the top 19 of the testing device housing 21. The tubular collector 11 is fed down a stabilizing receptacle 21 until the examination end 24 of the collector 11 located adjacent the end of the receptacle 21 and stopped from further downward movement by means of small stop members 25 at the examination end of the receptacle 21 that radiate inwardly from the interior wall surface of the receptacle.

Located slightly upwardly from the examination end 25 is a thin, highly transparent, round specimen collection examination tray 43 upon which the specimen of cough discharge falls and is collected for optical examination by a microscope 18.

Also, contained in the housing 21 are the electronic components that are employed to examine the specimen and determine whether it contains sign that the person is infected with the particular test or tests being run. These electronic components may be pre-mounted to a floor 31 during manufacture and then installed through an open bottom of the housing 21 and secured by suitable screw fasteners 27. Extending downward from the bottom surface of the bottom are four shock absorbing, resilient support pads to reduce vibration within the interior of the housing 21. A battery installation door (now shown) is also located in the bottom the enable installation and removal of a battery power supply.

Also, on the exterior of the housing are indicator lights 27 and 29 for indicated low battery level beneath a preselected operational level and whether full power has been turned on to all the electronic components needed testing, and lights 31 and 33 to indicated whether the collector has been fully installed or not. Power is applied by means of a push button, momentary contact switch 33, and data is entered and test results are shown on an electronic display with a touch screen keyboard.

The display, whether carried by the housing 12 or located in a remote-control unit, will have means to enter, such as a touch screen 102 upon which an interactive keyboard 103 may be used to enter test data. The test data preferably appears in six different windows: test name window 98; results window 94; test subject's name window 95; results window 94; date window 96; time of test window 98; and test location window 100.

A HDMI female connector 35 and USB connector 37 are provided at a rear side 39 of the housing for data receipt and transmission via hardwire, and a USB female receptacle 39 and a coaxial female receptacle 41 are provided for recharging a battery power supply. A handle 43 is provided to facilitate secure hand carry of the testing device.

Referring now to Fig., the collector 11 is seen when removed from inserted relationship with the testing device 13. At the collection end 9 is a is a cylindrical cap 49 with a round top closure 51 and downwardly extending walls _____ that snugly resiliently embrace the side walls of the collector to hold the top closure 51 in place. Alternatively, the inside surface of the downwardly extending wall 53 is provided with screw threads that mate with screw threads carried around the top of the body of the collector 11, and the cap 57 is screwed onto the collection end 9.

In any event the cap 51 is attached to the collector body during manufacture in a sterile, contamination-free environment and 51 is not removed until immediately before the cough discharge is to be collected. Then, as soon as the test charge is collected, the cap 51 is reattached to seal the open end and remains attached thereafter.

Mounted within the interior of the of the collector adjacent to and slightly recessed inwardly from the open examination end 53 of the collector 11, is mounted in a thin, highly transparent, circular specimen examination tray, or examination tray, 63, having a top surface upon which the cough discharge is collected 63. The sample tray is made of a highly transparent material and may be provided with a coating to promote visibility.

After the cough discharge is received within the tubular collector 11 and fallen onto the top surface of the examination tray 63 and after the cap 51 reattached, and before the collector 11 is installed into the testing device 13, a contamination preventing, thin foil-like seal adhered to the bottom edge of the collector 11 is removed to enable the microscope 63 to move into the open end to closely examine the specimen through the transparent plate 43. The thin seal is removed manually by gasping a short, radially outwardly extending pull tab 57 and peeling off the body of the seal 55 off of the ends of the bottom edges of the walls of the collector 11.

Once this is done, the collector 11 is installed into and secured in an examination position within the collector receptacle 21.

Preferably, the collector 11 including the cap 51 and the seal 55 are made from biodegradable material, and is discarded after being used only once. Alternatively, the collector 11 is made from a light weight, noncorrosive metal, such as aluminum, that can easily be cleaned and sterilized, refitted with a new cap 51 and seal 55 and used again.

Figure 3:
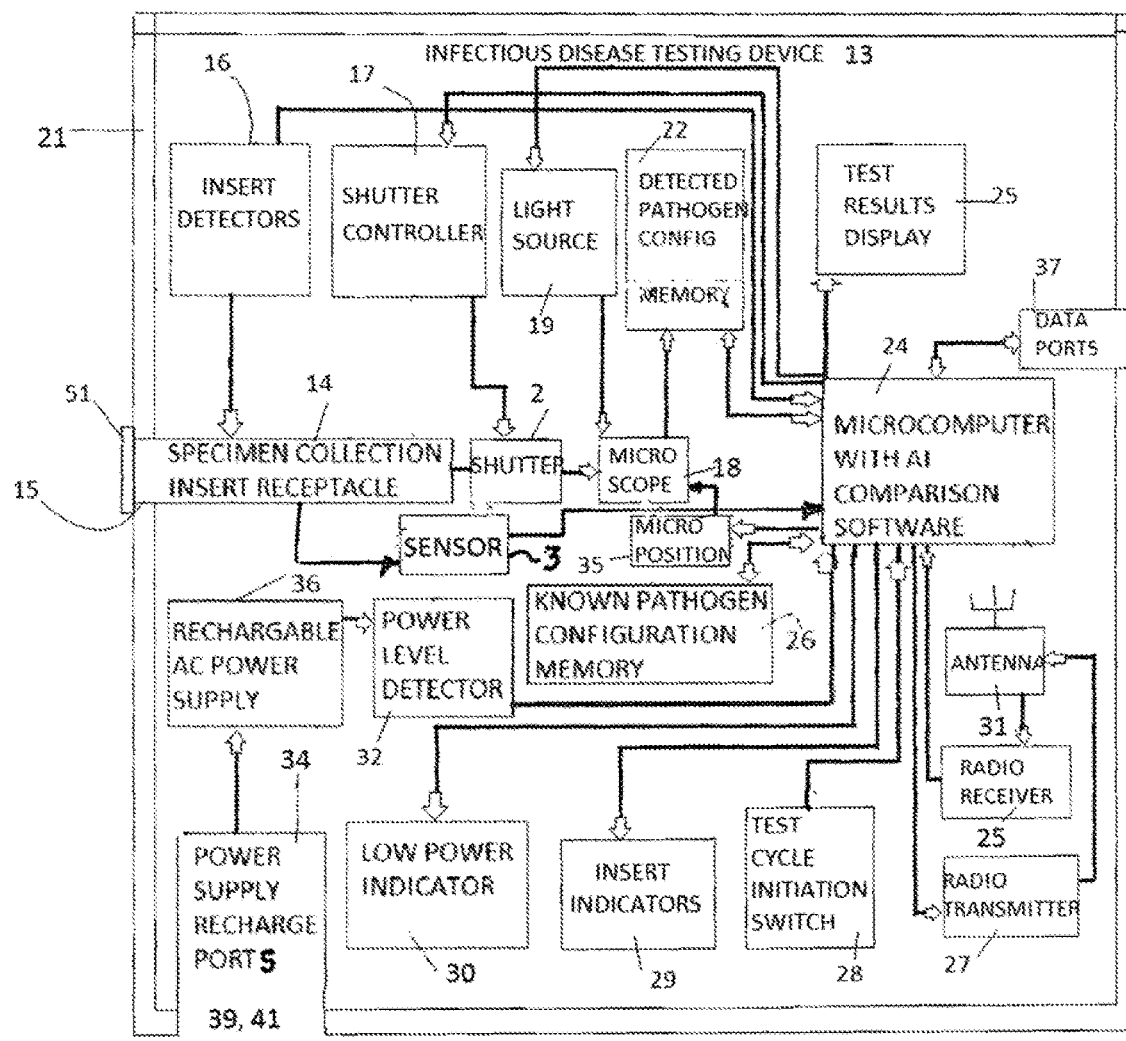
FIG. 3 is a functional block diagram of the infectious disease testing device, or testing device, of the present invention.

Referring to FIG. 3, a surrounding outer wall 12 of the housing 21 of the testing device 13, the various operational elements of the testing device 13 as shown and described below. The housing walls 12 may be made from molded plastic or metal. If made of thin walled plastic, a composite housing may be provided by the addition of an inner housing (not shown) made from elongate members in a cage-like configuration to strengthen the surrounding outer wall 12 and to provide greater protection of the operational elements.

Located at the leading end of, and surrounding, the leading edge of objective lens of the microscope 18 and located closest to the specimen examination tray is a high intensity LED light source 17 in the fowl of a circular string of LED's wrapped around the objective lens.

Figure 4A:
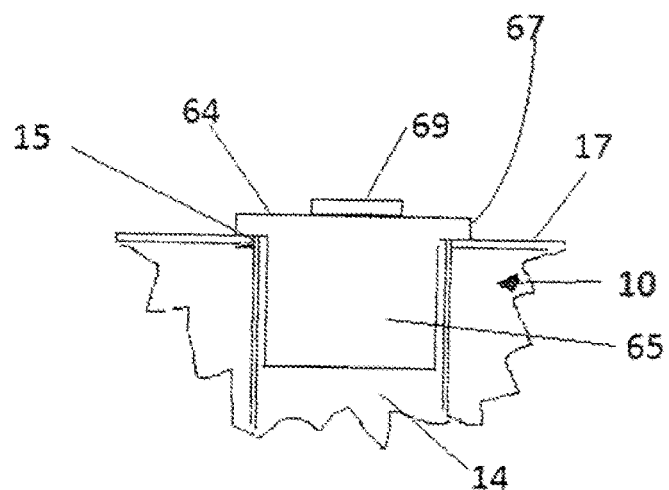
FIG. 4A is partial sectional side view of the testing device adjacent the collector receiving port and showing the port closure member installed whenever the collector is not installed as shown in FIG. 1, to prevent contamination of the interior of the testing device housing.
Figure 4B:
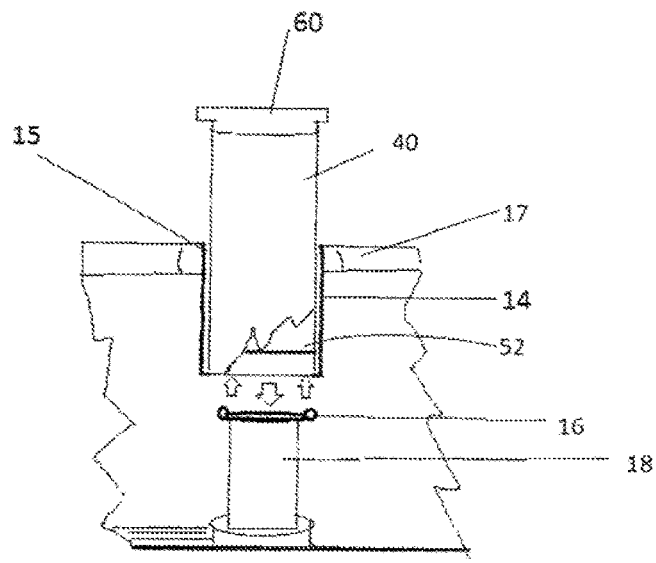
FIG. 4B is a sectional side view of the collector installed into an examination receptacle with the examination end seal removed and with the objective lens of the microscope and ring of target illumination LEDs surrounding the lens in an examination position to view through the bottom of the transparent examination tray the specimen supported on the top surface of the tray.
Figure 4C:
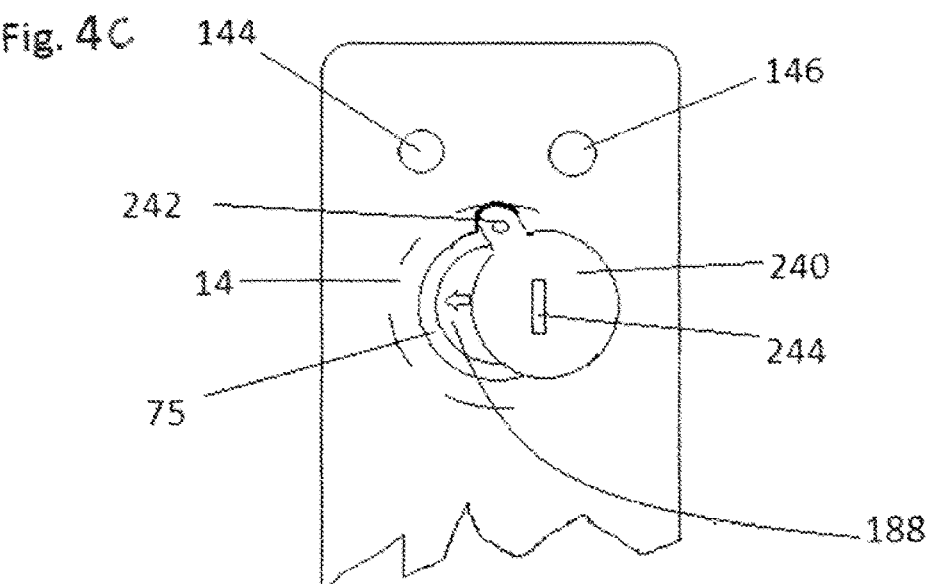
FIG. 4C is a plan view of the top surface of the testing device showing an alternative closure for the collector port opening which is pivotally attached to the housing to prevent loss.

Referring to FIG. 4B, when an examination of the specimen is to occur, the microscope 18, while carrying the LED light source ring 17, is moved through the open examination end 24 by means of a focus mechanism 35 controlled by the microcomputer 24 when running software responsive to resolution and quality characteristics of images received from the microscope 18 through the detected pathogen configuration memory 22. Snug enclosure of the light ring and objective lens by the cylindrical walls of the objective lens to the examination tray and the closeness of the collector to the objective lens protects against light aberrations, light leakage, reflections and other like distortion causing effects.

The intensity of the light and color spectrum generated by the light source 17 is established by a light source drive circuit 19 under control of the microprocessor controller 24 based on the quality of imaging being received. The light is preferably in the visible blue light spectrum but may be changed, as needed for clarification of the targets. The light from the light source passes through the bottom surface to the transparent 43 tray to illuminate only the bottom surfaces of the targets carried by the specimen supported on the top surface of the examination tray 43. Preferably, the top surface of the tray 43 is not illuminated and the interior surface of the collector 11 is covered with a non-reflective, black, light absorbing surface, such a conventional flat black paint during this "dark field" examination. Preferably, the top surface of the tray 43 is flat but could have or convex spherical shape to concentrate or to distribute and disperse the specimen Preferably, means are provided to keep the forward-most and exposed objective lens of the microscope 18 as clean as possible. In addition to use of the closure cap 5, seal 55 and the closure plug 51, a lens cleaning shutter 21 and a shutter controller 17 with a linear actuator arm attached to the shutter 21 are provided. As seen in FIG. 3, adjacent the bottom of the collector 11, a shutter 37 is provided. The shutter 37 has a coating of soft lens cleaning brushes that are carried on one side of the shutter 21 facing the objective lens.

Upon completion of each test, microprocessor 24 commands the shutter controller 17 to close and to protectively cover the entire surface of the objective lens and, in the process of so doing, wipe the objective lens with the soft lens cleaning brushes clean. The shutter 21 remains closed until the commencement of the next test when it is moved to an open opposition to enable specimen viewing and to again clean with the soft lens cleaning brush.

The microscopic assembly 18 has a magnification factor sufficient identify target elements in the specimen that indirectly indicate the presence of infection from pathogens or the presence of the pathogens, themselves. Mold spores are larger than bacterial pathogens which, in turn, are larger than viral pathogens. The magnification ratio, or factor, of the microscope 18 is controlled by the microcomputer 24, and may be varied to optimize visualization of being examined, the magnification of the microscope 18 from approximately ×60 to ×100, as may be needed for sufficient clarity sufficient to discern individual and group configurations and other identifying factors of any target pathogens.

In the case of visualizing a virus, per se, the magnification factor is at least 100× but less for por identifying an infectious bacterium, the magnification factor is less for an infectious mold spore. Preferably, the magnification factor is sufficient to detect all three different types of infectious pathogens themselves or signs of their presence. If a microscope with a fixed magnification is not used, the focal length is controlled is changed as needed by means of a focus mechanism. The microcomputer controls the magnification based on clarity, or lack thereof, of visual depictions taken from the microscope and 18 and temporarily stored in digital form in a detected pathogen configuration sensor memory 22.

Figure 5:
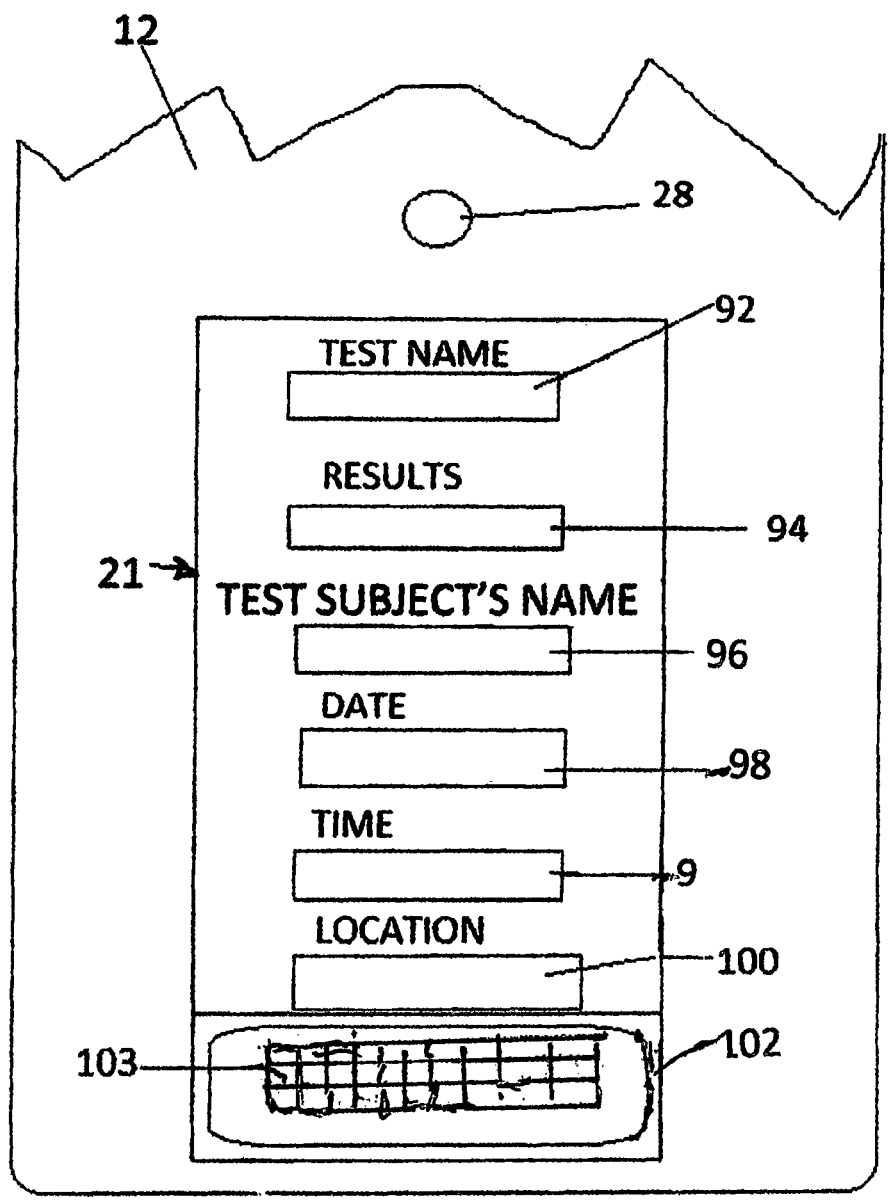
FIG. 5 is a plan view of the electronic display 25 of FIG. 3.

Referring to FIG. 5, the microscope assembly 18 has a magnification factor range of approximately 60× to 100× with a dry, achromat objective lens. numerical aperture of 0.85 with a working distance of 0.3-8 mm, a parfocal length of 45 mm and a 24 mm center width. The microscope assembly 18 also has a correction capability to compensate for sample tray refractive and classified as infinity Referring to FIG. 5, the microscope assembly 18 has a magnification factor in the approximate range of 60× or 100× The objective lens 135 is a dry (no oil immersion) achromatic infinity lens infinity type with a numerical aperture of 0.85 with a working distance of 0.3-8 mm, a parfocal length of 45.0 mm and a 24.0 mm center width. The microscope assembly 18 also has a correction capability to compensate for sample tray refractive properties and classified as infinity.

A center axis of symmetry 137 of the objective lens 135 and all the other elements of the microscope assembly is aligned with the microscopic assembly 18 when fully installed in the receptacle 14. The microscope assembly 18 may follow industry Mechanical Tube Length (MTL) standards used in the microscopy industry. Use of this industry may cause aberration and focusing issues, as described below with reference to FIG. 6, in accordance with the present invention such problems are mitigated by using focusing software and deconvolution applications.

While not necessary, the microscope could be a mini-microscope using a microchip as a magnifier and detector. Also, scanning with signals of selected frequencies can result in a small virus emitting an identifying signal which could be used for identification in lieu of optical comparisons.

The microscopic examination process advantageously is label-free and no stains, dyes or markers to promote fluorescence. The light used to illuminate the specimen and targets therewithin s preferably a blue light with a wave length of approximately 450 nm wavelength. The illumination energizes electrons in the specimen which then elevate to a higher state among fluorophores which, in turn, emitting signals of light from the specimen.

LED is the preferred method of fluorescence due to its low heat emission and longevity in use. Images will be taken on a Monochrome 1.4 Megapixel CCD (Charged Coupled Device) at 6.45 Micron pixel using a 1392×1040 Jpeg format. Monochrome will be used because it provides sharper images over color.

A successful test cannot be conducted unless there is adequate electrical power to do so. Accordingly, a power level detector 35 monitors the rechargeable DC power supp 36, and if power falls beneath a preselected level, reports this low power condition to the microprocess 24. So long as the power is beneath this preselected level, the microprocessor 24 will not allow performance of a test. A low power indicator 32, such as the low power indicator light or an indication of low power is provided at the display 21 to notify the user, who must then recharge the battery 36 through one of the recharging ports 39 or 41. Alternatively, if no source of recharging electrical power is available, the depleted battery may be removed and replace with another rechargeable battery that is fully charged or an equivalent, fully charged, non-rechargeable battery.

Attempted test performance is also prevented if an insert detector does not detect that a collector 11 has been fully installed in the receptacle 14 and that the seal 55 has been removed. One or more full installation detectors 16, such as photodetectors, metal detectors or microswitches may be used. The same types of detectors used for the full installation detector 16 may be used for a seal detector 15.

Alternatively, when a test initiate order is given by the microcomputer, the microscope may be used to determine whether the cap has been removed or not, such as by observing a black letter "X" placed on the outside of the slip. In accordance with the method of the present invention, tests that are merely prevented from proceeding should not be reported as being indeterminate During the conduction of a test, after the microscope has been properly focus for optimum picture quality results, one or more visualizations, or photographs, of the configurations and location of potential pathogen targets, or other distinctive identifying signs, are stored, at least temporarily, in the in the detected pathogen memory 22. The microprocessor then compares the photograph of the unknown pathogens to one or more known configurations of those that are stored in the known configuration memory 26. The photographs of relevant known pathogen indicators that are prestored for comparison in pathogen configuration memory 26, are preferably built by an artificial intelligence technique known as deep learning in which the computer views multiple images, makes a decision of infectious, or not infectious, and is repetitively corrected when wrong until only right decisions are made.

Once all the photographs from the memory 22 have been acquired, they are compared to selected one or ones of the photographs stored in the known pathogen memory. After sufficient time has passed to complete the comparison or comparisons, the microcomputer actuates the display 21 to indicate one of three possible results. Test results indications can also be provided by energizing light of different colors coded to the different results.

In any event, the three possible results are "POSITIVE", (i.e. pathogen sign identified), NEGATIVE (i.e. pathogen not found) or "INDETERMINATE" (i.e. Insufficient confidence in either a positive or a negative result). Preferably, a percentage of level of confidence in accuracy of the report test results is ascertained based on known statistics about the relevant pathogen.

While the testing device may be embodied in the form shown in FIG. 1, there are different forms that may be best used in different commercial, economic, social, national or reginal environments. The unit show 13 shown in FIG. 1 is suitable to be operated in a fully self-contained environment and in an environment in which air wave communication may also provide advantages. Accordingly, for purposes of airwave communication, an airwave antenna 31 connected to a radio signal receiver 25 and a radio signal transmitter 27. Both the receiver 25 and the transmitter 27 are connected to the microprocessor.

This radio signal capability can be advantageously used in a number of ways. First, the start of the test can be controlled remotely by a separate multiuse control unit, such as a cellular telephone, electronic tablet, laptop computer, etc. If such a multiuse controller had a display screen, then the display 21 on the unit 10 shown in FIG. 1 could be eliminated.

If the start of the test begins automatically in response to all the test preconditions being satisfied, or if the test initiation is achieved via remote control, then the start switch 28 can be eliminated except for emergency use. The switch 28 may be used in the event, due to climactic or other conditions prevent the receipt of radio signals by the testing device 13.

More importantly from a public health point of view, with radio communication, a remote computer with vastly greater computing power for comparisons of known and unknown pathogens could be conducted with both greater accuracy and speed, and would be enabled to poll all units in an epidemic or pandemic area. In formation could be gathered from around the world via satellite communication, hot spots reported, etc. that will enable both health authorities and individuals deal successfully with the circumstances.

In any event, the comparison of known with unknown begins when a start test signal is received by the microprocessor 24, either through actuation of a switch or a signal from a remote controller, or the unit is programmed to automatically start once all the preconditions noted above have been satisfied. When the testing device 13 will be used by multiple users, it is preferred that a test cycle not begin until the name of the test subject or perhaps the date and other information has been entered are made into memory associated. Likewise, the testing system is only capable of testing for a single disease, then there will be no need to enter he name of the test, since the name can be presumed.

In that case, the start test switch 28 is be used only as a backup in case airwave signals are not coming in for some reason, sunspots, or another. Additionally, as a safety factor, even if the system 10 is capable of receiving function commands through the airwave, if a user (maybe owner) wishes to run the test regardless, whether or not, all requested information has been entered. Perhaps, language bathers, illiteracy, disability, or the very symptoms of the disease that is to be the subject of the test, prevents entry of the data required.

In any event, if a test is initiated the comparison occurs in response to actuation of the switch 28, only if the collector 11 is received and fully installed within the receptacle 14, as indicated by one or more insert detectors 16, and only if there is sufficient electrical. DC power for target illumination, focusing, and the like, as monitored by the power level detector 32 to be capable of running a successful testing provided as indicated by and DC electrical power being provided from a rechargeable DC power supply that is connected to all the electronic components via suitable power supply connections 38 is above a preselected minimum level needed for successful operation of the testing system device 10. If the power level is beneath the preselected level needed for operation, the microprocessor 24 actuates a low power indicator 30 that may be a light, sound or visual display of power level. If a display is used, then it may provide an indication of power levels in excess of the minimum level.

After comparison and analysis, the microprocessor 24 energizes a test results display 25, which may be used to enter test data such as name and name of test to provide an indication of the test results, indicating whether the test has been positive or negative, and if positive and more than one pathogen is being tested for, an indication of what pathogens were detected. The display may also provide the date and location of the test. Preferably, the past test results shown on the display are stored for future reference to be downloaded or displayed at a later time. After examining the display, the user may again actuate the switch 28 to clear the display. However, preferably avoid power waste, the display 21 be cleared automatically after a sufficient viewing delay time has passed and the unit 13 turned off.

After the collector 11 is removed completely from the receptacle, or if another insert has been installed in the receptacle 14 but not fully installed, then each actuation of the test cycle initiation switch will bring up on the display 21, or remote display on a cellphone or electronic notebook, the results from prior tests, successively, for each past test still stored in the microprocessor 24.

Referring to FIG. 4A, whenever the collector 11 is not within the receptacle 14, the entry port opening 15 is sealed closed 15 with an anti-contaminant plug 64 with a plug body 65 and a transverse annular cap 65 that radially extends outwardly from top of the plug body 65. The bottom surface of cap 65 rests on a mating raised annular ridge 67, and a gripping handle 69 extends upwardly from the center of the cap 65 to the top surface of the housing 12. Preferably, the cap 65 is secured to the housing by a flexible tether or the like to prevent loss.

Figure 6:
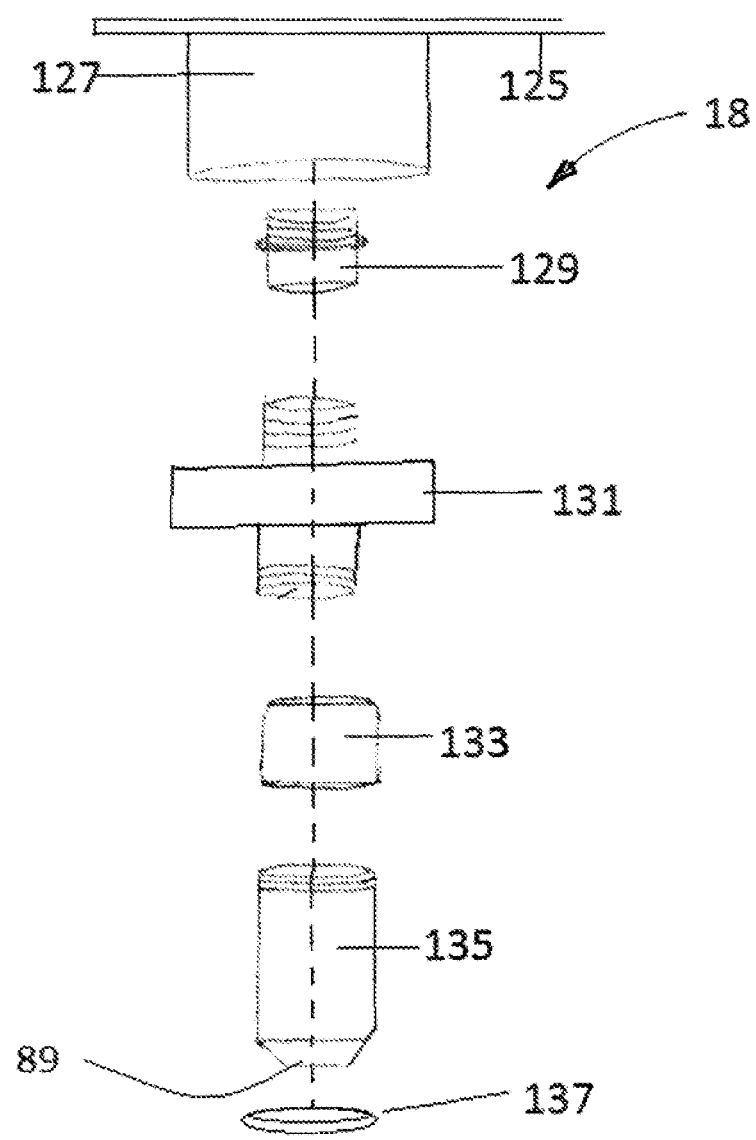
FIG. 6 is an exploded view of the microscope assembly o24 of FIG. 3.

As seen in FIG. 6, in addition to the objective lens, the microscope assembly 18, a tube lens 133 which is used to further magnify the image from the objective lens 135 to clarify the image seen by the objective lens 135. The tube lens 133 is used in conjunction with the infinity objective lens for image creation. The tube lens 233 has a tubular housing with an approximate length of 10 mm with an image circle approximately 25 mm.

Next to the tube lens 133, is located a focus drive mechanism 131 for moving the objective lens 135 and the tube lens 133 along the central axis as needed for image clarification, as may be determined by the microprocessor 24.

Figure 7:
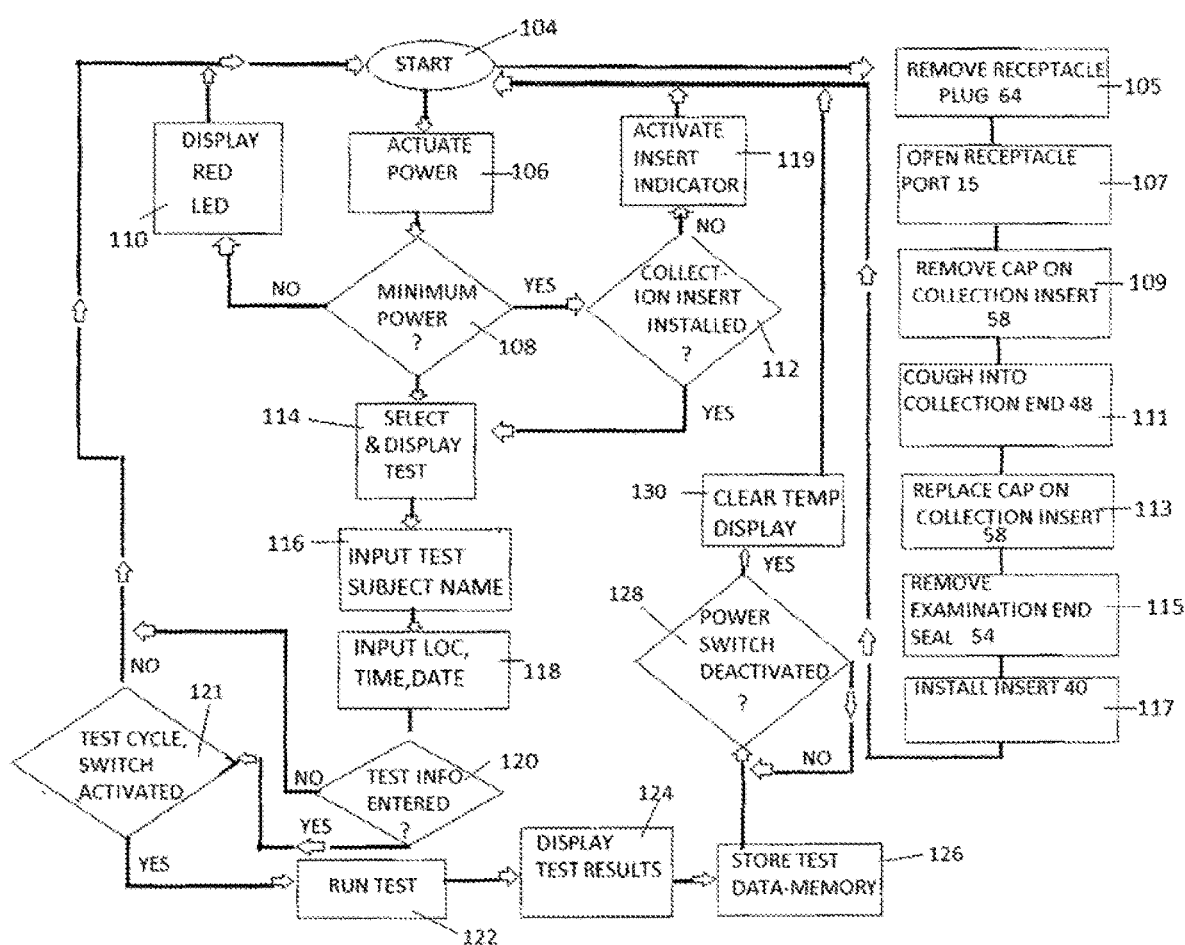
FIG. 7 is a logic flow chart showing the operation of the testing device of FIGS. 1 and 3.

Referring to the flow chart of FIG. 7, the operation by a user of the test device begins, after start 104, by the user first manually removing the collector 40, from the receptacle 14, if being carried within the test device 10 if carried apart from the test device 10, then the collector 40 is removed from any contamination preventing envelope within which it may be contained.

If removed from the receptacle 14, in the next step 107, receptacle port 15 is closed with the closure member 64, FIG. 4A. Next, in step 109, the collector insert plug 60 is removed from the collection end of the collector 11. The test subject then coughs through the now exposed open collection end 24 and into the tubular body 42(?) in step 111. After the cough into the collection insert 40, the collection insert plug 60 is reinstalled to close the collection end against entry of contaminants. Then in step 115, the seal 50, FIG. 3B, is removed from the examination end of the collection insert 40, and the collection insert 40 is inserted back through the receptacle port 15 and into the receptacle 14 in position for examination.

Once all this specimen collection and preparation is completed the test sequence can be commenced. First, in step 106 the full power switch is actuated to provide power to all the operative elements besides the low power detector 32 and low power indicator 30, FIG. 1. In action step 108, if the power level is too low for successful operation of a test cycle, then the low power indicator 30 is actuated and the program returns to start 104. If power is above the preselected power level, then in decision step 112 a decision is made whether the collection insert 40 has been fully and correctly installed. If not, then the no insert indicator is activated and the program returns to start 104. If the collector 11 is correctly installed, then the user may proceed to step 114 and select the name of the test that is desired, and then, in step 116, enter the name of the test subject. In step 118, the date, time and location of the test is entered.

Then in decision step 120 a determination is made by the microprocessor as to whether all of the test information, particularly the subjects name and test name, is entered. If all the test information is not present the program returns to start. If all test information is present, the program moves to decision step 121 where it is decided if the test cycle initiation switch 28, FIG. 1, has been actuated. If so, then in step 122 the high intensity light source 16 is energized, the microscope is focused, the configuration images are stored, compared and otherwise analyzed.

Upon completion of analysis, in action step 124, the test results (Positive, Negative or Undetermined) are displayed and then in step 126, the test results and related information is stored in a results memory (not shown) of the microprocessor 24. When the full power and test initiation switch is again actuated, in step 130, the display is cleared and another test cannot be conducted until removal of the collection insert 40 of the test previously conducted.

Figure 8:
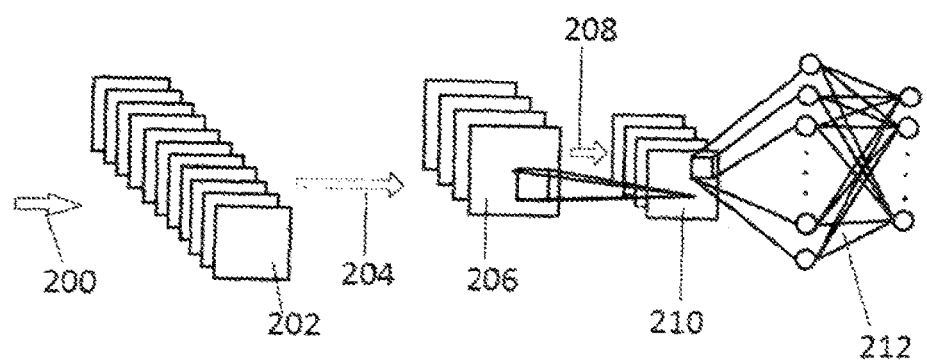
FIG. 8 is a schematic illustration of the convolution of the pooled images of specimens with disease indicators and known to be from infected test subjects and those being examined.

As seen in FIG. 8, images 200 of (known or unknown) pathogen visual indicators are passed to individual labelled input files convolutions 204. Convolution 204 of these images are then passed in step 204 to pooling input files, pooled in step 208. They are passed to pooled output files 210, which in turn, creates connected or pooled representations of the pooled images.

In the present invention, the detection of a specimen pathogen configuration stored in the detected configuration memory 22 corresponding to a known pathogen configuration stored in the known pathogen memory 26, an architecture developed by Google and known as Mobilenet—SSD is employed.

Figure 9:
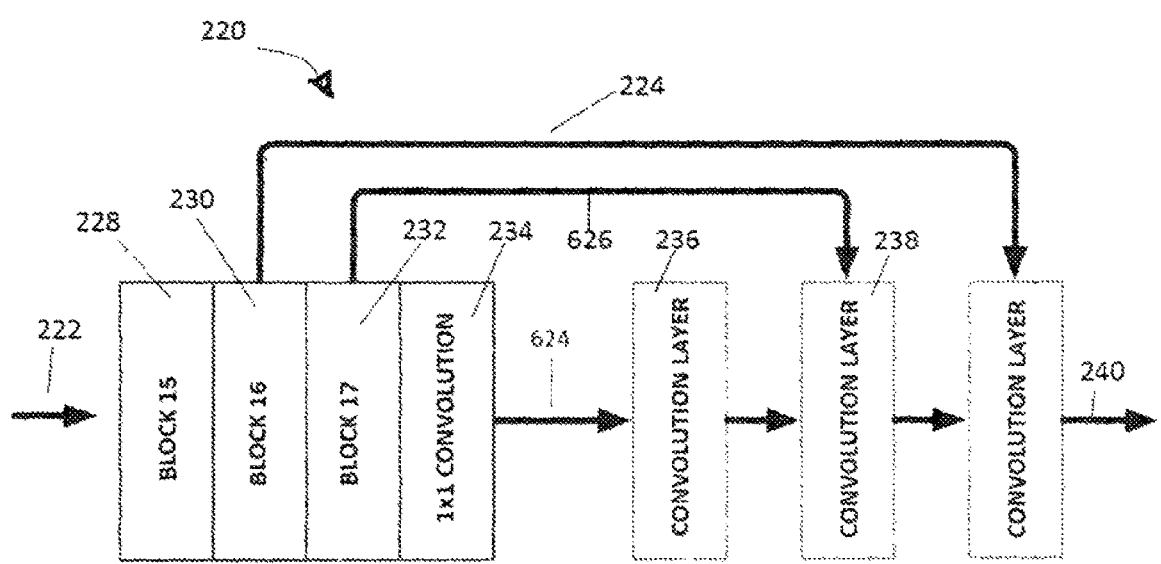
FIG. 9 is a schematic of pooled photographs being convoluted in isolated files.
Figure 10A:
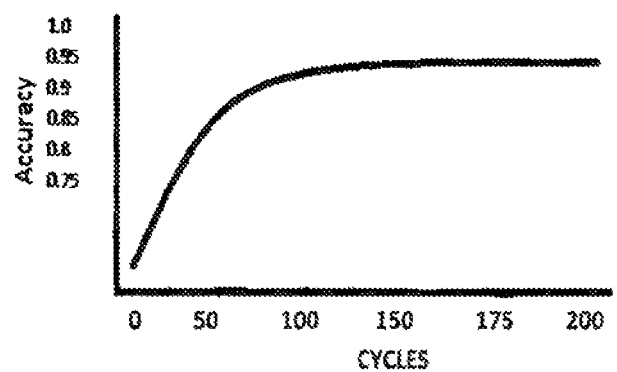
FIGS. 10A and 10B illustrate the manner in which accuracy increases and data loss decreases with increases in the number of processing cycles of the photographic files of FIGS. 8 and 9.
Figure 10B:
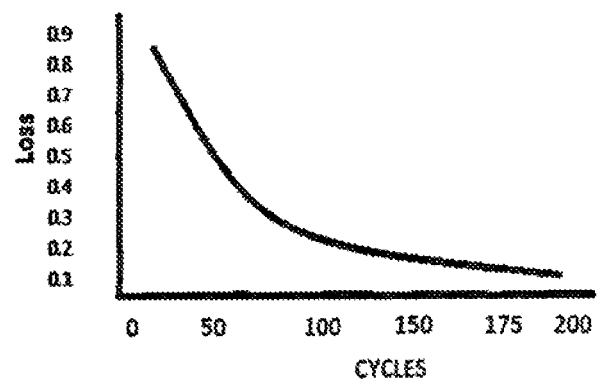
Figure 11:
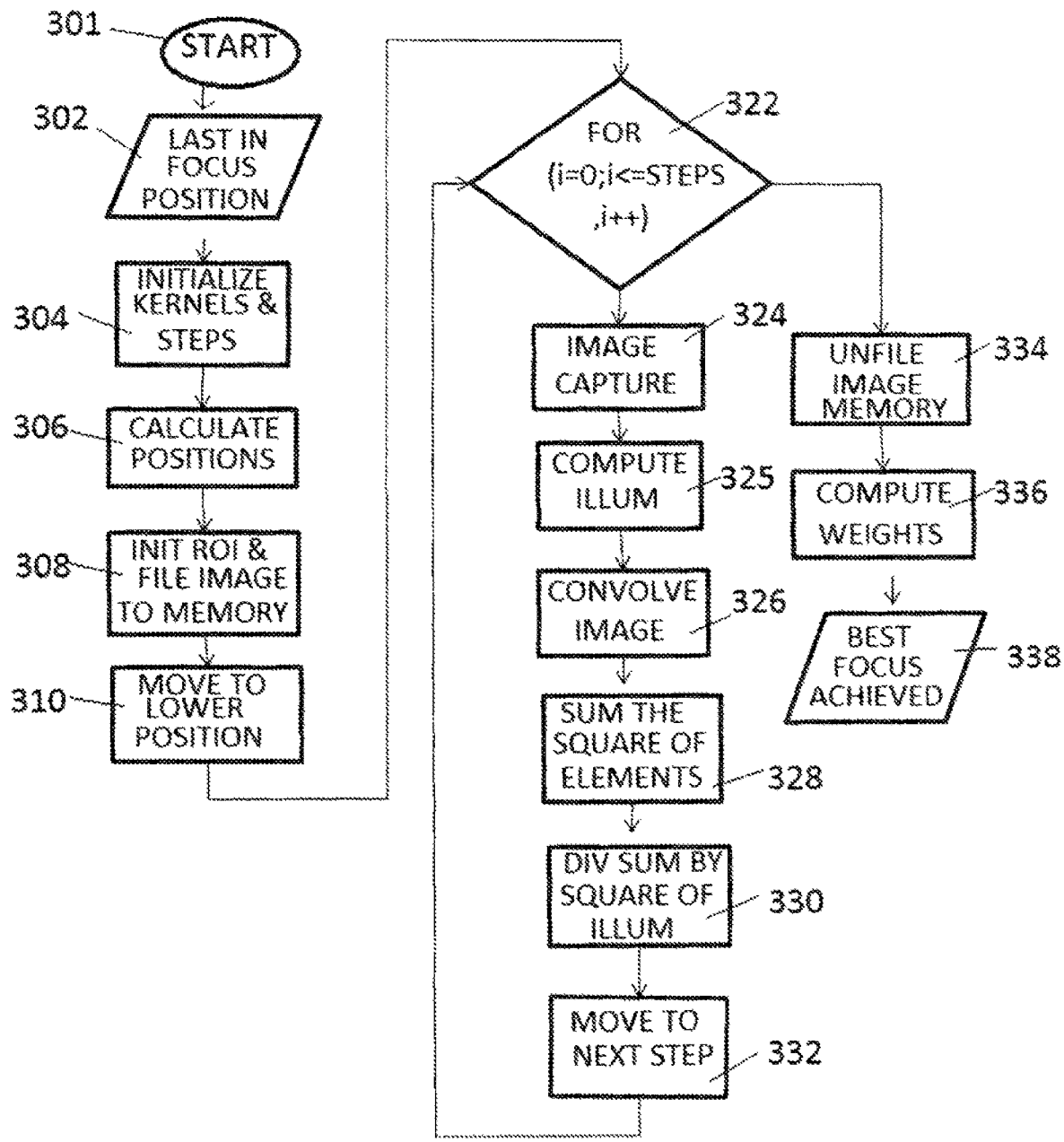
FIG. 11 is a flow chart illustrating focus control of the microscope of FIGS. 1, 3 and 6.

Referring to FIG. 9, a data flow structure of the image pooling process model FIG. 8 that may be employed in the present invention is illustrated so that only a single image is required for detection and faster speed, increased accuracy, multiple predictions and performance on resource-contrain devices is acquired.

A network is employed that is known as a convolutional neural network, or CNN. A convolution is the simple application of a filter to an input that results in an activation. Repeated application of the same filter to an input results in a map of activations called a feature map, indicating the locations and strength of a detected feature in an input, such as an image. One model in particular used in image processing is called a region based convolutional neural network, or R-CNN.

This system looks for patterns in images by assigning filters and using a mapping process, progressively in each layer which is optimized with different parameters for different tasks then becomes more sophisticated as the system progresses toward a prediction. Popular examples of this science are used in autonomous vehicle operation and facial recognition technology. Other deep learning platforms for object detection include YOLO (You Look Only Once) and SSD (Single Shot Multi-box Detector).

As seen in FIG. 8, convolutions 204 of images 200 from the microscope 18 are stored in input memory locations 202 and then passed to 206 and then pooled at 208 and 210 to provide a final output 212. The pooling process averages out or generalizes the multiple inputs. This may be done by averaging coordinates of pixels of a multiplicity of photographic images to reach an image that is generally representative of all of the salient features of the specimen.

In the present invention, the detection of a specimen pathogen configuration stored in the detected configuration memory 22 corresponding to a known pathogen configuration stored in the known pathogen memory 26, an architecture developed by Google and known as Mobilenet—SSD is employed.

Binary codes such as Java, C++ or Python are preferably used to interface and execute functions throughout the object detection process including establishing parameters, accessing repositories and files, and establishing classifications and confidence/loss values.

The detection process employed by the present invention is preferably Tensorflow API, which is an open-source software program developed by Google, as a library that is driven in C++ script in conjunction with Anaconda's Python script. This process creates a dataset or retrieves a preprocessed dataset for detecting objects in an image generated by the microscope 18 and stored in the specimen configuration memory 18. Tensorflow, utilizing Mobilenet and SSD models, provide the framework for the detection process employed by the test device 10. Tensorflow, Mobilenet and SSD models, needed computer script, and datasets are all available on the internet from a variety of repositories and downloads free of charge.

The first phase of Tensorflow is deciding on a dataset to use and one that contains collected images that are trained and tested through a model in order to establish a learning phase for that particular model. There are numerous datasets available to the public but one in particular that is widely used is called COCO through Microsoft In the present invention, a custom dataset is required due to the uniqueness of the images that will be necessary. If appropriate data sets can be found, then the use of such available datasets is preferred because then, the laborious task of labeling and training and processing of collected images necessary in building a dataset, explained below.

Figure 12:
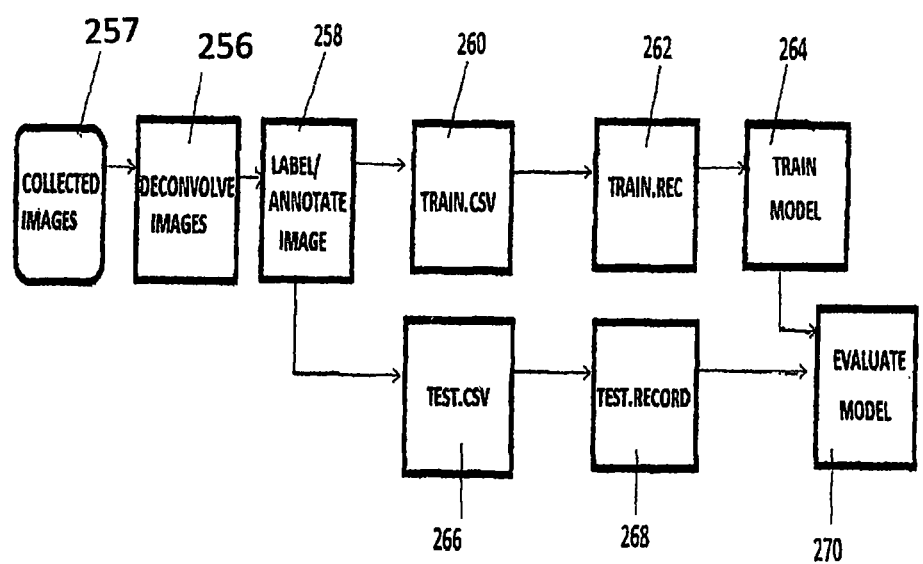
FIG. 12 is a flow chart of how the know specimen photographic standard, to which comparison of collected specimens are made to make a test result determination, are acquired, tested and evaluated.

The steps used to build the custom data set in accordance with the present invention is illustrated in FIG. 12 including the steps of annotating, training/testing and lastly the evaluation process necessary in building the custom dataset. First, in step images of pathogens are collected. This collection is achieved by obtaining samples from random infected individuals, as many as ten or more, who have been diagnosed as being who are infected with the pathogen of interest to be detected. This preferably achieved by having the infected person cough onto the specimen collection insert, although licking the specimen collection insert or swabbing it on the inside of a person's cheek may also be employed. COVID 19, through coughing. In the case of coughing, the specimen is captured on the specimen tray at the end of the elongate tubular body of the collector 11, shown in FIG. 2A.

Referring to FIG. 12, the process to create a custom dataset through the use of Tensorflow is illustrated. First, in step 257, a plurality of digital images, as many as one hundred, are captured of each specimen from all ten or more individuals for a total of one thousand digital images to be used in the custom dataset. Then in step 258 the one thousand images are processed via the deconvolution process described above to remedy any degradation in the images.

Next, in step 260, an image labeling and annotating function is performed on the one thousand collected images, This requires a bounding box to be created for areas of interest in each image that allows focus only on relevant target objects from an image. Multiple bounding boxes are allowed in one image. This procedure establishes classification and x-y axis coordinates of the target(s) of interest. The targets of interest in infected samples will be classified and determined by comparing samples, obtained in similar manner, but only one hundred images will be captured from individuals that are not infected with a pathogenic disease. Thus, the test is performed for only detecting target objects associated with a pathogenic virus. There is no need to detect targets that are not disease-causing pathogens. Afterwards, in steps 262, 264 and 266 training of the model occurs. Then finally in step 272, the model is evaluated following the test 268 and test record 270 have been established.

In step 260, the image labeling and annotating function includes creation a bounding box for areas of interest in each image that allows focus only on relevant target objects from an image. Multiple bounding boxes are allowed in one image. This procedure establishes classification and x-y axis coordinates of the target(s) of interest. The targets of interest in infected samples will be classified and determined by comparing samples, obtained in similar manner, but only one hundred images will be captured from individuals that are not infected with a pathogenic disease. Thus, the test is performed for only detecting target objects associated with a pathogenic virus. There is no need to detect targets that are not disease-causing pathogens. Afterwards, in steps 262, 264 and 266 training of the model occurs. Then finally in step 272, the model is evaluated following the test 268 and test record 270 have been established.

Images can be deconvolved in 2D or 3D, but 2D deconvolution, although sacrificing a degree of quality in the output, is less taxing processing needs. Deconvolution software called DeconvolutionLab provided by Biomedical. Imaging Group uses 2D deconvolution and is more than sufficient for the purposes of this invention. This platform is linked to a variety of imaging platforms, and hosts numerous algorithmic models to choose from. Each of the algorithmic models have their own strengths and assumptions tailored for specific areas of distortion so applying different models may be necessary in order to achieve a desired output.

Figure 13:
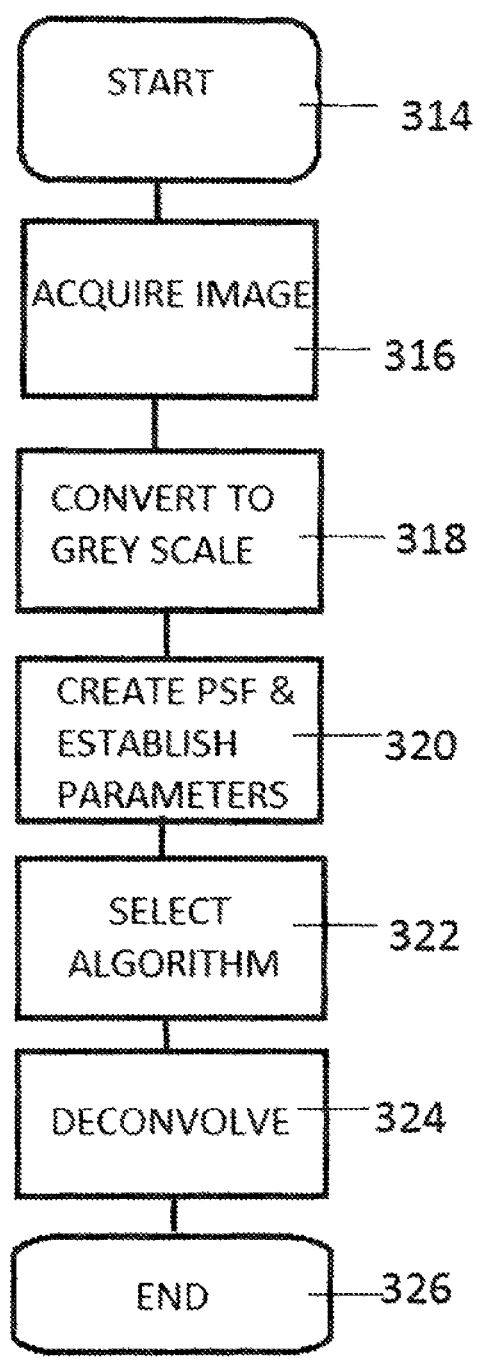
FIG. 13 is a schematic flow chart illustrating the steps taken to prepare either a standard or collected photographic file including the step of converting the file to gray scale for easier analysis and clarity.

Referring to FIG. 13, after start 314, the computational process of a single image, begins at step 316 with acquisition of the image which is then converted to an 8-bit greyscale in step 318. Next in step 320, the point spread function (PSF) describes the response of an imaging system to a point source or point object. A more general term for the PSF is a system's impulse response, the PSF being the impulse response of a focused optical system.

In particular, the PSF needs to be determined either experimentally or theoretically. The PSF can be determined using software known in the industry as a PSF generator. In this function, parameters are key in the creation. Once a general PSF has been created it is used on all images inputted through the model.

Parameters needed to define the PSI include the refraction index of media used. Refractive index is the measure of bending of a light ray when passing from one medium to another. If the sample tray 43 is only 0.17 mm thick and 25-mm in diameter, a refractive index of "1.51" will result.

The other parameters that need to be known include the numerical aperture of the objective lens to be used, such as, 0.85 na, the wavelength of light source, such as 450 nm Blue LED, estimated as zero, pixel size of the and CCD camera being used. In the case of a 6.45 micrometer pixel 107.5.

If slice spacing is needed, then the width of the image in pixels is "1392", the height of the image in pixels "1040" and the number of images in a stack is one and the normalization value is one.

Preferably, the algorithm that is selected in step 426, FIG. 13 is Tikhonov models will be utilized due to its efficiency with the conditional variables of this application and its high probability to remedy degradation imposed by this optical systems imaging platform.

Finally, the images are deconvolved in step 428, the image saved, and the end 326 of the process is completed.

Referring to FIG. 12, the process to create a custom dataset through the use of Tensorflow is illustrated. First, in step 257, a plurality of digital images, as many as one hundred, are captured of each specimen from all ten or more individuals for a total of one thousand digital images to be used in the custom dataset. Then in step 258 the one thousand images are processed via the deconvolution process described above to remedy any degradation in the images.

Next, in step 260, an image labeling and annotating function is performed on the one thousand collected images. This requires a bounding box to be created for areas of interest in each image that allows focus only on relevant target objects from an image. Multiple bounding boxes are allowed in one image. This procedure establishes classification and x-y axis coordinates of the target(s) of interest. The targets of interest in infected samples will be classified and determined by comparing samples, obtained in similar manner, but only one hundred images will be captured from individuals that are not infected with a pathogenic disease. Thus, the test is performed for only detecting target objects associated with a pathogenic virus. There is no need to detect targets that are not disease-causing pathogens.

Afterwards, in steps 262, 264 and 266 training of the model occurs. Then finally in step 272, the model is evaluated following the test 268 and test record 270 have been established.

The comparison of infected and non-infected samples looks for abnormal or atypical subcellular markers, in cough discharge, between infected and non-infected samples. Detecting subcellular behavior and aberrations of cells, molecules, mucus, saliva are measured through criteria such as morphology, geometric configuration, grouping/pattern/cluster and spectral analysis to detect unusual characteristics found in infected samples.

Morphology criterium relates to identification of any unique structure/form or mutation of innate cells or structures due to the introduction of a foreign body.

Geometric configuration criterium will identify shapes of interest of a foreign body.

Grouping/Pattern criterium will identify behaviors of a foreign body or innate defenses effects on a foreign body or any particularities of subcellular activity.

Spectral criterium will identify variations in grey scale of both foreign and natural bodies.

All or only a few or one of these criteria may be employed to recognize whether a specimen from a test is carrying or otherwise suffering from one or more of the following diseases or health conditions: severe acute respiratory syndrome (SARS), middle eastern respiratory syndrome (MERS), Covid-19 (SARS-CoV-2), influenza, lung cancer, tuberculosis, human immunodeficiency virus (HIV), multcillin-resistant staphylococcus aureus, hepatitis, pneumonia, legionnaires' disease, vancomycin-resistant enterococci (VRE), pertussis (whooping cough), swine flue (H1N1), bird flu (Avian Flu H5N1, bronchitis, respiratory syncytial virus (RSV) and enterovirus.

Once images are available for a dataset, training and testing a model is performed with the collected images as necessary to establish a learning curve. The collected images are split between two different memories with eighty percent of the one thousand images in one memory that will be trained, while only twenty percent of the images in the other memory will be used for testing. This uneven treatment is necessary because more images are needed for training a model as possible. This platform measures loss/accuracy results through the training and evaluation process and self optimizes itself as iteration occur until an acceptable loss and accuracy level is achieved. The more epochs (times through model) the lower the loss gradient becomes and higher the accuracy is achieved. Ultimately, this weighs the model predictions against the ground truth boundary boxes established earlier.

The network that is employed in the present invention is known as a convolutional neural network, or CNN.] A convolution is the simple application of a filter to an input that results in an activation. Repeated application of the same filter to an input results in a map of activations called a feature map, indicating the locations and strength of a detected feature in an input, such as an image. One model in particular used in image processing is called a region based convolutional neural network, or R-CNN. This system looks for patterns in images by assigning filters and using a mapping process, progressively in each layer which is optimized with different parameters for different tasks then becomes more sophisticated as the system progresses toward a prediction. Popular examples of this science are used in autonomous vehicle operation and facial recognition technology. Other deep learning platforms for object detection include YOLO (You Look Only Once) and SSD (Single Shot Multi-box Detector).

As seen in FIG. 8 convolutions 204 of images 200 from the microscope 18 are stored in input memory locations 202 and then passed to 206 and then pooled at 208 and 210 to provide a final output 212.

In the present invention, the detection of a specimen pathogen configuration stored in the detected configuration memory 22 corresponding to a known pathogen configuration stored in the known pathogen memory 26, is achieved by using architecture developed by Google and known as Mobilenet—SSD is employed.

The network shown in FIG. 8, is known as a convolutional neural network, or CNN. A convolution is the simple application of a filter to an input that results in an activation. Repeated application of the same filter to an input results in a map of activations called a feature map, indicating the locations and strength of a detected feature in an input, such as an image. One model in particular used in image processing is called a region based convolutional neural network, or R-CNN. This system looks for patterns in images by assigning filters and using a mapping process, progressively in each layer which is optimized with different parameters for different tasks then becomes more sophisticated as the system progresses toward a prediction. Popular examples of this science are used in autonomous vehicle operation and facial recognition technology. Other deep learning platforms for object detection include YOLO (You Look Only Once) and SSD (Single Shot Multi-box Detector).

As seen in FIG. 8 convolutions 204 of images 200 from the microscope 18 are stored in input memory locations 202 and then passed to 206 and then pooled at 208 and 210 to provide a final output 212.

In the present invention, the detection of a specimen pathogen configuration stored in the detected configuration memory 22 corresponding to a known pathogen configuration stored in the known pathogen memory 26, an architecture developed by Google and known as Mobilenet—SSD is employed.

Referring to the flow chart of FIG. 14, after image capture in step 348 and deconvolution in step 350, the image is passed for analysis. In step 352, the AI software is initiated and receives images from the dataset memory 354 of known specimens and begins to analyze the sample. In decision block. 358, if a determination as been made that a sample is not suitable for analysis a report of an indeterminate test result is provided. If the sample is suitable, then a decision is made at decision step 360 whether the confidence score is greater or equal to 80%. If it is, then process moves to step 364 to provide a negative test report. On the other hand, if the confidence level is not less than or equal to 80%, then in step 368 a positive test report is provided.

While a detailed description of a preferred embodiment of the invention, it should be appreciated that it may be embodied in many different forms. Further relevant information may be obtained from the provisional patent application upon which this application is based, as noted above, and which is hereby incorporated by reference.

The system may be most cheaply produced in a basic form for individual, personal use in which case it is capable of detecting only a single type of infection of greatest concern and in which test results may be indicated solely by colored indicator alights, and all testing analysis is conducted within the testing device without airwave communication with a remote and powerful computer for image analysis.

It may be provided with both local analysis capability and the ability to communicate with a remote computer in case of need for additional processing capability but in the event airwave communication is not possible due to weather, distance, sunspots, etc.

The testing device need not necessarily be portable, such as being AC outlet power capable for use at the door of a school, public building, store, etc. to make sure that everyone who enters is disease free and not merely without fever or other symptoms of infection. Discovering that the are infected after having entered the building with close ventilation and social gathering is to late to stop the spread.

The collector is preferably elongate buy only as much as may be needed to be functional. Preferably, to match the shape of modern microscopes the collector housing.

Preferably, the collector is cheaply made from biodegradable material and is intended to be discarded ager only one use, Alternatively, it is made from thin wall aluminum and may, commercial sterilization, resold or otherwise distributed.

It should be appreciated that while the present invention has been disclosed with reference to collecting a specimen through cough discharge, the invention is capable of working with other sources of specimens such a blood, urine and fecal material, with slight modification. A drop of blood, urine or suspended fecal material could easily be dropped through the collector inlet to fall onto the examination tray and the known memory would store photographs of the appropriate type of specimen for comparison and detection.

If further information is desired with respect to any of the features of the invention or the science and technology upon which it is based, reference should be made to the following journal and other articles, all of which are hereby incorporated by reference.

Plos One Journals, by Zhendgizng Xu & Fangxia Sehn et al." Molecular and microscopic analysis of bacteria and viruses in exhaled breath collected using a simple impaction and condensing method", 7-2012;

NCBI, NIH, Sattar Farzan, Cough and sputum production, Chapter 38

ARXIV, M. Pohiker, Ovid Kruger,etal, Respiratory aerosols and droplets in the transmission of infectious disease;

PUBMED, NIH, Robert Witte & V. Andriasyan, et al., Concept of light microscopy of viruses, April 2018;

Lightscience, Nature, Lin Li & Wei Guo, et al., Label-free super-resolution imaging of adenoviruses by submerged microsphere optical nanoscopy, 2013;

The Scientist, Jef Akst, "Artificial intelligence sees more in microscopy than humans do", May 2019;

MC, NIH, Said Agrebi & Anis Larbi, "Use of artificial intelligence in infectious diseases", March, 2020.

ResearchGate, R. Subramanian, "Recognition of Pathogens using image classification based on improved and recurrent neural network with. LSTM"., May, 2019;

Scientific Reports, Nature, Claire Chen & Ata Monjoubfar, et al., "Deep learning in label-free cell classification", March, 2016;

Nature Communications, Nature, Artificial intelligence for the detection of COVID-19 pneumonia on chest CT using multinational datasets, August, 2020;

Journal of Integrative Biology, Mary Ann Liebert Publishing, A. Swan & S. Liddell, et al., "Application of Machine learning to proteomics data: Classification and biomarker Identification in post genomics biology", November 2013;

Wired, Will Knight, "AI algorithms are slimming down to fit in your fridge", December, 2020.

Pubmed, NIH, Sawako Enoki, et al, "Label-free singleparticular imaging of the influenza virus by objectivetype total internal reflection dark-field microscopy", 2012;

India Today, Ashish Pandey, IIT—"Hyderabad develops world's smallest microscope", June, 2021.;

Microbe Notes, Segar Aryal, "Dark-field microscope— Definition, principle and uses", July, 202;

PMC, HHS, V. Pansare & S. Hejazi, et al., "Review of the long-wavelength optical & NIR imaging materials: Contrast agents, fluorophores and multi-functional nano carriers";

Journal of Proteome, ACS Publications, "Label-free selected reaction monitoring enables multiplexed quantitation of S100 protein isoform in cancer cells";

PMC, NIH, Yang Liu & Jianquan Xu, "High-resolution microscopy for imaging cancer pathobiology", September 2020;

MDPI, Emma Touizer & Christian Sieben, et al., "Application of super-resolution and advanced quantitative microscopy to the spatio-temporal analysis of influenza virus replication", January, 2021:

Scientific Reports, Nature, Felix Junger & A. Rohrbach, et al., "Fast, label-free super-resolution live-cell imaging using rotating coherent scattering (ROCS) microscopy";

Scientfici Reports, Nature, Ugar Aygun & H. Urey, et al., "Label-free detection of nanoparticles using depth scanning correlation interferometric microscopy", June, 2019;

CNET, Elizabeth Moore, "Nanoscope makes live viruses visible for first time", March, 2011;

India Today, "Coronavirus under the microscope: A closer look at the deadly pathogen";

Nanowerk, "Microsphere nanoscope enables super-resolution biological microscopy", January 201;

Science Daily, Bill Kisliuk "Smartphone microscope can detect a single virus, nanoparticles", September 2013;

Physicsworld,, Anna Demming, "Optical microscopy— How small can it go?", October 2020.;

Focalplane, "Compact and high performance fluorescence microscopy, " April, 2021 .:

Pubmed, NIH, Feilong Cao & Kaixuan Yao, e "Deconvolution neural network for image super-resolution", December 2020;

Eurasip Journal, Han Yu & Ting-Zhu Huang, et at, "Super-resolution via a fast deconvolution with kernel estimation, July 2016";

JJOURNAL OF PHYSICS, F. Sroubek, "Simultaneous super-resolution and blind deconvolution", 2008;

Spie, M. Toscani & Sandra Martinez, et al., "Single image deconvolution with super-resolution using the SUPPOSe algorithm", February 2019.;

OSA Publishing, Zhishen Tong & Zhentao Liu, etal, "Preconditioned deconvolution method for high-resolution ghost imaging", 2021.;

IEEEXPLORE, S. Harmeling & Suvrit Sra, et al., "Multiframe blind deconvolution, super-resolution, and saturation correction via incremental EM"2010;

Scientific Reports, Eitan Edrel & G. Scarcelli, "Memory-effect based deconvolution microscopy for super-resolution imaging through scattering media", September 2016;

Reference should be made to the claims with regard to the breath and scope of the present invention and the impact it may have during not only worldwide pandemics, but during flew season, etc.

* * * * *

The invention claimed is:

1. An infectious disease testing system for deter mining whether a test subject is infected with a pathogen, comprising:

a specimen collector having a hollow body extending between a collection. end and an examination end with a specimen receipt opening at the collection end of the hollow body for receiving, within the hollow body, a specimen of bodily fluids coughed or otherwise exhaled from the mouth of the test subject through the specimen receipt opening, a transparent specimen collection tray carried by the hollow body adjacent the examination end for direct receipt of an specimen having no additions, alterations or treatments or any kind, after passing though the hollow body from the collection end; and an electronic testing device requiring no delay for treatment of the specimen before the test can be performed., having a protective housing, with an interior and a collector receipt opening, for releasable receipt of the examination end and at least a portion of the hollow body adjacent the examination end, into the protective housing, and means including microscope within the protective housing to form at least one enlarged magnified visual image of the specimen collected and having no treatment displayed on the collection tray;

means including a local microcomputer within the protective housing responsive to the at least one enlarged magnified visual for determining whether the at least one magnified enlarged visual image of the specimen having no additions, alterations or treatments or any kind, contains any indications of infectious disease; and means responsive to the local microcomputer to provide an indication of whether the at least one magnified enlarged visual image contains any indications of infectious disease.

2. The disease testing system of claim 1 including a removable closure member for closing the specimen receipt opening except when opened to receive a specimen from the test subject.

3. The disease testing system of claim 1 including a removable seal at the examination end of the hollow body for protectively covering the transparent specimen collection tray against contamination after a specimen has been collected from a test subject but before the examination end of the collector has been slidably inserted into the protective housing through the collector receipt opening for visual examination of the specimen on the specimen collection tray.

4. The disease testing system of claim 1 in which the determining means includes a remote microcomputer located externally of the protective housing, and communication means for two-way communication between the local microprocessor and the remote computer.

5. A disease testing device for determination from a specimen collected form a test subject which has not been treated whether a test subject has a disease for which the test subject is being tested, comprising:

a protective housing with a collector receipt opening for releasable receipt of a specimen collector, having a hollow body with a collection end and an examination end, when the examination end has a specimen obtained from oral exhalations of a test subject through an opening at the collection end and passing through the hollow body of the specimen collector to the examination end;

collected with no treatment a collector receptacle within the protective housing aligned with the collector receipt opening in the protective housing for sliding receipt the tubular specimen collector into engagement with the receptacle for securely holding the examination end specimen at a precise, stationary examination location;

a light source within the housing for illuminating the specimen at the examination end of the collector when received within the housing and being securely held within the receptacle;

means including a microscope with an objective lens for obtaining a magnified view of a configuration to the collected specimen at the examination end of the collector;

a digital camera for making at least one magnified high-resolution digital photograph of the magnified view of the collected specimen at the examination end of the collector;

a collected configuration memory for storing the at least one high-resolution digital photograph;

a known pathogen configuration memory for storing a high resolution digital picture of a configuration at least one known specimen of at least one known disease obtained from a person known to have the known disease;

means including a local microprocessor for comparing the digital photograph of the collected specimen stored in the collected specimen configuration memory with the high resolution digital photograph of the at least one known specimen; and means responsive to the comparing means for providing an indication of whether or not the configuration of the known specimen corresponds to the configuration of the collected specimen.

6. The disease testing device of claim 5 in which the examination end of the specimen collector has a specimen access opening, and carries a transparent specimen collection tray visually accessible through the access opening; and the light source includes a ring of LEDs surrounding the objective lens of the microscope having a size enabling both the ring and the objective lens to be inserted into the examination end of the collector to illuminate the specimen collection tray.

7. The disease testing device of claim 5 including
means for detecting when at least one precondition required for initiating a successful test is not satisfied, and
means responsive to the detecting means to prevent initiation of a test.

8. The disease testing device of claim 5 in which the comparing includes the use of AI software with means for performing at least one pooling, convolution, deconvolution and deep learning process to determine whether the configuration of the known specimen corresponds to the configuration of the collected specimen.

9. The disease testing system of claim 1 in which the software of at least one of the at least one of the local computer and the remote computer employs an artificial intelligence program that compares images of known images of infectious disease with the images of the specimens to determine a match indicating that the specimens represent images of infectious disease.

10. A specimen collector forming part of a disease testing system for determining whether a test subject is infected with a pathogen,
said collector being releasably being releasably insertable into the housing the disease testing system, said testing system including
an electronic testing device having
a housing,
a microscope to form magnified enlarged visual images of the specimen,
an examination port hole for receipt of at least an examination end of the collector housing into an examination location at which the specimen can be viewed by the microscope to form at least one magnified enlarged visual image, and
a local microcomputer with
software responsive to the at least one enlarged visual image to determine whether the at least one magnified enlarged visual image contains any indications of infectious disease, or
software capable of communicating the at least one visual image to a remote computer with software responsive to the at least one visual image to make a determination of whether the at least one visual image contains any indications of infectious disease and reporting back said determination to the local computer, and
means responsive to the local computer to provide an indication of said determination,
said specimen collector, comprising:
a housing with a tubular body,
a specimen receipt opening at a collection end of the tubular body for receiving, within the tubular body, a specimen of bodily fluids exhaled from the mouth of the test subject;
an examination opening at an examination end of the tubular body located oppositely of the specimen receipt opening;
a specimen collection tray carried by the tubular body adjacent the examination end; and
a readily removable anticontamination seal attached to the examination end of the tubular body to protectively close the examination opening to protect the collection tray from contamination; and
an examination port hole for receipt of at least the examination end of the collector housing into an examination location at which the specimen can be viewed by the microscope to form the at least one magnified enlarged visual image.

11. The oral specimen collector of claim 10 including means for releasable sealing closed the specimen receipt opening except when being used to receive a specimen from the test subject.

12. The oral specimen collector of claim 10 including a readily removable anticontamination closure member attached to the housing to close the specimen receipt opening except when slidably receiving the specimen collector.

13. The oral specimen collector of claim 10 including means for releasably sealing closed the examination opening.

14. A method of exclusively using only an electronic disease testing device for determining whether a test subject is infected with the disease, said electronic disease testing device having
a protective housing having an interior containing means for visually examining and optically determining whether a specimen is indicative of an infectious disease,
means carried by the protective housing for providing an indication of said disease,
a collector opening in the housing for releasable receipt of a specimen collector containing the specimen into the interior, said specimen collector having
a tubular body extending between a collection end and an examination end,
said collection end having a specimen receipt opening for receiving, within the tubular body, a specimen of bodily fluids coughed or otherwise exhaled from the mouth of the test subject through the specimen receipt opening for passage through the tubular body to the examination end for receipt onto a transparent examination tray, comprising the steps of:
removing a contamination prevention closure from e specimen receipt opening of the specimen collector;
having a test subject cough or otherwise exhale a specimen from the test subject's mouth and lungs into the specimen receipt opening;
conveying the specimen through the tubular body to the transparent examination tray for visual display for optical examination of the specimen from an exterior side of the examination tray opposite an interior side upon which the specimen is received;
after receiving the specimen onto the examination tray removing a contamination cover from the examination end of the collector protecting the examination end and the exterior side of the transparent examination tray; and
after removing the contamination cover from the examination end of the collector, slidably fully inserting the collector through the collector opening to enable visual examination of the specimen.

15. The method of claim 14 including the steps of
reattaching the contamination prevention closure to the specimen receipt opening of the specimen collector after the test subject has coughed or otherwise exhaled a specimen from the test subject's mouth and lungs into the specimen receipt opening to protect the collected specimen against contamination and leaving the contamination prevention closure attached to the specimen receipt opening of the specimen at least until visual examination of the specimen.

\* \* \* \* \*